United States Patent
Gerold et al.

(10) Patent No.: US 9,074,269 B2
(45) Date of Patent: *Jul. 7, 2015

(54) MAGNESIUM ALLOY

(75) Inventors: Bodo Gerold, Zellingen (DE); Heinz Mueller, Erlangen (DE); Joerg Loeffler, Zürich (CH); Anja Haenzi, Baden (CH); Peter Uggowitzer, Ottenbach (CH)

(73) Assignee: BIOTRONIK VI Patent AG, Baar (CH)

( * ) Notice: Subject to any disclaimer, the term of this patent is extended or adjusted under 35 U.S.C. 154(b) by 1537 days.

This patent is subject to a terminal disclaimer.

(21) Appl. No.: 11/691,754

(22) Filed: Mar. 27, 2007

(65) Prior Publication Data

US 2007/0227629 A1   Oct. 4, 2007

(30) Foreign Application Priority Data

Mar. 31, 2006   (DE) .......................... 10 2006 015 457

(51) Int. Cl.
    *C22C 23/06* (2006.01)
    *C22C 23/00* (2006.01)
    *C22C 23/04* (2006.01)

(52) U.S. Cl.
    CPC ................. *C22C 23/00* (2013.01); *C22C 23/04* (2013.01)

(58) Field of Classification Search
    USPC .................... 148/420; 420/402–406, 411–412
    IPC .............................................. C22C 23/00,23/04
    See application file for complete search history.

(56) References Cited

U.S. PATENT DOCUMENTS

| | | | |
|---|---|---|---|
| 3,334,998 A * | 8/1967 | Fisher | 420/405 |
| 3,419,385 A | 12/1968 | Foerster et al. | |
| 5,073,207 A * | 12/1991 | Faure et al. | 148/667 |
| 5,248,477 A | 9/1993 | Green et al. | |
| 2003/0183306 A1 | 10/2003 | Hehmann et al. | |
| 2006/0246107 A1* | 11/2006 | Harder et al. | 424/426 |

FOREIGN PATENT DOCUMENTS

| | | | |
|---|---|---|---|
| AT | 251893 | | 1/1967 |
| DE | 1239105 | | 11/1967 |
| DE | 1248306 | | 3/1968 |
| DE | 1953241 | | 5/1971 |
| DE | 2658187 | | 6/1977 |
| DE | 19915277 | | 10/2000 |
| EP | 0219628 | | 5/1990 |
| EP | 0 407 964 | | 1/1991 |
| EP | 0 531 165 | | 3/1993 |
| EP | 1419793 | * | 5/2004 |
| GB | 1035260 | | 7/1966 |
| GB | 1067915 | * | 5/1967 |
| GB | 1075010 | | 7/1967 |
| GB | 1525759 | | 9/1978 |
| JP | 06316750 | * | 11/1994 |
| JP | 8134581 | | 5/1996 |
| JP | 9041065 A | * | 2/1997 |
| JP | 2004099941 | | 4/2004 |
| JP | 2005213535 | | 8/2005 |
| WO | 2005123972 | | 12/2005 |

OTHER PUBLICATIONS

Hort et al; Intermetallics in Magnesium Alloys; Advanced Engineering Materials; 2006; pp. 235-240; 8, No. 4.

* cited by examiner

*Primary Examiner* — Sikyin Ip
(74) *Attorney, Agent, or Firm* — Greer, Burns & Crain, Ltd.

(57) ABSTRACT

A magnesium alloy having Y, Zn, Ca, Mn, Ag, Ce, Zr, or Si. The alloy is distinguished in that, in the event of suitable treatment, the alloy is convertible into a very fine-grained microstructure, in particular, having grain sizes less than 20 μm. The alloy components are not or are hardly toxicologically relevant.

21 Claims, No Drawings

MAGNESIUM ALLOY

PRIORITY CLAIM

This patent application claims priority to German Patent Application No. 10 2006 015 457.6, filed Mar. 31, 2006, the disclosure of which is incorporated herein by reference in its entirety.

FIELD OF THE INVENTION

The present invention relates to a novel magnesium alloy and its use as well as an associated production method for the magnesium alloy.

BACKGROUND OF THE INVENTION

Numerous magnesium alloys of greatly varying composition and usability are known. For purposes of the present invention, the term magnesium alloy is primarily understood to include a group of alloys which, in addition to magnesium as the main component, contain additives (typically up to approximately 10%) of aluminum, manganese, zinc, copper, nickel, cerium misch metal and other rare earth metals, silver, zirconium, silicon, etc. Magnesium alloys are divided into magnesium wrought alloys (typically based on Mg—Mn, Mg—Al—Zn) and magnesium cast alloys; the magnesium cast alloys are subdivided by sand casting, chill casting, and die casting or according to alloy components. Magnesium alloys may be processed according to most known metallurgical primary forming and reshaping methods.

The alloy additives decisively determine the properties of the metallic material. It is known, for example, that aluminum contents greater than approximately 10 weight-percent result in brittleness of the alloys. Zinc and especially zirconium increase the toughness, while manganese improves the corrosion resistance. Beryllium additives of a few parts per million significantly reduce the tendency of the molten metal to oxidize, but are undesirable because of their toxicity. Rare earth metals and thorium increase the heat resistance. The melting point of the alloys is typically between 590° and 650° C.

The main areas of use of magnesium alloys are aviation, mechanical engineering of all types, optical devices, electrical technology, electronics, means of transportation, office machines and domestic appliances, and, in general, areas in which strength and rigidity at the lowest possible weight are important and low manufacturing costs in large productions are required. Magnesium alloys are receiving increasing significance in engine construction for motor vehicles. A special application relates to the use of biodegradable magnesium alloys in medical technology, in particular for vascular and orthopedic implants.

A limitation of known magnesium alloys particularly comprises the ductility of the material, which is inadequate for specific processing methods and intended uses. One approach for improvement may be in reducing the grain size of the metallic microstructure (fining). Fining comprises all metallurgical measures which result in a small grain size of the alloy. In general, this requires an increase of the number of nuclei in the melt during solidification or in the solid body due to finely dispersed precipitates. Fining has an advantageous effect on the mechanical properties, in particular the ductility of the alloy. Very small grain sizes have been achieved until now only in the small preparative scale in the field of magnesium alloys, for example, by ECAP/ECAE methods (ECAP is equal channel angular pressing; ECAE is equal channel angular extrusion). The cited methods may not be implemented in large scale, however; up to this point, only small volumes (a few $cm^3$) of extremely fine-grained alloys have been produced, predominantly using the technical magnesium alloy AZ31. Findings of a generally valid nature about the alloy components required for fining or even their proportion in magnesium alloys have only been available in inadequate form up to this point.

Therefore, there is a persistent need for magnesium alloys which permit fining even using typical large-scale methods. Furthermore, there is a need for a magnesium alloy whose grain size is reduced for improved ductility in relation to typical alloys. Moreover, there is a need for a preparation method for a fine-grained magnesium alloy which may be technically implemented in larger scale. Finally, in regard to ecological aspects and also a use of the alloys in medical technology, it is necessary to select the alloy components under toxicological and/or biocompatible aspects; the biocompatible aspects, in particular, while avoiding the aluminum present in many magnesium alloys.

DETAILED DESCRIPTION OF THE INVENTION

A first exemplary embodiment of the present invention relates to a novel magnesium alloy of the following composition:
Y: 0.5-10
Zn: 0.5-6
Ca: 0.05-1
Mn: 0.05-0.5
Ag: 0-1
Ce: 0-1
Zr: 0-1 or Si: 0-0.4
the specifications relating to weight-percent of the alloy, and magnesium as well as contaminants due to production making up the residual component of the alloy remaining up to 100 weight-percent. The alloy is distinguished in that, in the event of suitable treatment, the alloy is convertible into a very fine-grained microstructure (in particular <20 μm). Furthermore, the alloy components are not or are hardly toxicologically relevant, so that, in particular, an application in medical technology appears predestined.

The present invention is based, inter alia, on the finding that the cited alloy components having the cited proportions impede the grain growth during hardening from the melt by their enrichment at the hardening front and, in addition, during the hot reshaping by the formation of intermetallic phases. In the event of a coarse-grained microstructure, the plastic deformation is dominated by dislocation movements on the basal plane and by twinning; in contrast, fine-grained magnesium microstructures allow the activation of prismatic and pyramidal gliding even at room temperature, which significantly improves the ductility of the material. The alloy components enriched at the hardening front during the hardening having high Q factor (grain growth restriction factor) delay the grain growth and contribute to a small grain size of the cast microstructure. The very small intermetallic phases provided in the solidified magnesium alloy of the composition, explained in greater detail below, influence the recrystallization during the hot reshaping of the cast microstructure and also significantly contribute to the fine microstructure formation. The presence of the intermetallic phases not only improves the ductility of the material, but also decisively influences the corrosion properties of the material. The corrosion properties of the material are significant, in particular, if the magnesium alloy is used to produce biodegradable implants (preferably stents). Typically, the presence of fine intermetallic phases (instead of coarse-grained phases) having special stoichiometry will increase the corrosion resistance. The goal is to produce a single-phase microstructure and avoid coarse multiphase microstructures.

Preferred magnesium alloys result through the following restrictions of the proportions of the specified alloy components or more than one of these alloy components (specifications in weight-percent):

Y: 4-8;
Zn: 0.8-2.5;
Ca: 0.05-0.2;
Mn: 0.05-0.25;
Ag: 0.05-0.6;
Ce: 0-0.5;
Zr: 0.3-0.7 or Si: 0.05-0.25.

The cited alloy compositions appear, according to first initial experiments and theoretical considerations, especially suitable for providing extremely fine-grained materials based on magnesium (in particular having grain sizes <20 µm). It is to be noted that zirconium and silicon are to be prevented from neighboring one another, because intermetallic phases which are unsuitable for the purpose of fining form from the two elements.

An alloy in the meaning according to the present disclosure relates to a metallic single-phase or multiphase material of a dual-material or multimaterial system, whose starting components (alloy elements) interact with one another metallurgically and result in the formation of new phases (mixed crystals, intermetallic compounds, superstructures). The magnesium alloy contains magnesium as the main component.

It is preferable, in particular in connection with the above-mentioned preferred composition variations of the magnesium alloy, for the magnesium alloy to contain one or more intermetallic phases comprising:
  (i) Mg and one or more elements selected from the group: Zn, Ca, Mn, Ag, Ce, Zr, Si, and Y; or
  (ii) 2 or more elements selected from the group: Zn, Ca, Mn, Ag, Ce, Zr, Si, and Y.

The presence of one or more intermetallic phases of the cited compositions is a significant index for the suitability of the alloy for producing a fine-grained material (preferably having a grain size <20 µm), if this alloy is not already provided as a fine-grained material. One or more intermetallic phases selected from the following group: $Ca_2Mg_6Zn_3$, $AgMg_4$, $Mn_2Zr$, $Zn_2Zr$, $MgZn_2$, and $Mg_{24}Y_5$, are preferably provided.

Intermetallic phases (compounds) are chemical compounds, present in the microstructure of alloys, made of two or more metallic elements, whose structure significantly differs from that of the metals forming them. In addition to cubic structures, tetragonal and more complex structures also arise. In addition to metallic, atomic and ionic bond components also exist in the lattice. Besides intermetallic phases having stoichiometric composition in accordance with the existing valences, there are also those in which this exact composition only represents a special case in a broad homogeneity range. This results from the tendency of the participating metals to form a lattice having the highest possible coordination number and packing density under the given bonding conditions. Metal bonding and properties are more strongly pronounced the higher the coordination number, e.g., in the group of Laves phases. Hume-Rothery phases form broad homogeneity ranges, as well as intermetallic phases having intercalation structures. In the event of growth of the homopolar and/or heteropolar bond components, the intermetallic phases crystallize in lattices having low coordination number, such as the Zintl phases. The melting points of the intermetallic phases are significantly higher than those of the metallic components, the electrical conductivity is significantly lower. Intermetallic compounds arising in metallic microstructures as phases may increase the strength in finely dispersed form or may result in brittleness of the alloy in coarser form; in addition, intermetallic compounds arising in metallic microstructures as phases may impair the corrosion resistance.

A volume proportion of the intermetallic phases of the magnesium alloy <2 volume-percent, particularly <1 volume-percent is preferable, in particular, in connection with the previously described exemplary embodiments. Alternatively or additionally, the following are preferable:
  (i) a grain size of the intermetallic phases <1 µm; and/or
  (ii) a grain size of the alloy <20 µm, in particular <10 µm.
For purposes of the present invention, the term "grain size" is understood as the mean value of the diameter of the crystallite present in a metallographic grind pattern.

Magnesium alloys of the above-mentioned exemplary embodiments have especially favorable properties in relation to typical magnesium alloys for processing and the ductility is significantly increased. Ductility (or also toughness, deformation capability) is generally understood as the capability of a metallic material to deform permanently under given conditions at sufficiently high mechanical stresses, before cracking occurs. This capability is of great significance for many components, since locally occurring mechanical tension peaks may only be dissipated by a ductile material without cracking by permanent deformation with simultaneous strain hardening. This feature makes the use of the magnesium alloys according to the present invention especially advantageous as the material of choice for biodegradable implants, especially for stents. In a given material, the ductility is a function of the temperature, the strain speed, the multiaxial nature of the acting mechanical tension state, and the environment. Parameters of ductility are, for example, the ductile yield and percent area reduction at fracture, the impact value, and the fracture toughness.

The magnesium alloy according to the present invention preferably has a tensile yield of A5 standard samples at room temperature of >20%. The ductile yield (elongation at tear, symbol $\epsilon_R$ or $A_5$) is the name for the percentage ratio of the length change $\Delta L$ (at the moment of tearing) to the starting length $L_0$ under a tensile stress.

A second aspect of the present invention relates to a method for producing a fine-grained magnesium alloy. In one exemplary embodiment, the method comprises the following steps:
  (i) providing a batch of the formula
    Y: 0.5-10
    Zn: 0.5-6
    Ca: 0.05-1
    Mn: 0.05-0.5
    Ag: 0-1
    Ce: 0-1
    Zr: 0-1 or Si: 0-0.4
  the specifications being in weight-percent of the batch and Mg and contaminants due to production making up the remaining residual component of the batch up to 100 weight-percent;
  (ii) primary forming of a magnesium alloy from the batch by casting; and
  (iii) reshaping the magnesium alloy by compression.

Using the method according to the present invention, it is possible for the first time to produce very fine-grained magnesium alloys in the industrial scale. The approach is distinguished in that reference may be made to experiential values from metallurgical methods known per se, and the development of an industrial manufacturing process is significantly simplified. The primary forming in step (ii) is preferably performed by continuous casting, since this method results in materials of higher homogeneity. Furthermore, it is preferable if the reshaping in step (iii) is performed by extrusion, in particular at a temperature in the range from 280° C.-350° C., preferably at a temperature in the range from 290° C.-320° C. If necessary, the batch composition is tailored to the preferred compositions already described in connection with the description of the magnesium alloy.

For purposes of the present invention, casting relates to a manufacturing method in which the materials are poured in liquid or pulpy state into a prepared cavity (casting mold), which forms the negative of the cast part to be cast. The materials solidify in the casting mold and reproduce the cast part as a positive. The solidification occurs through hardening of the metallic melt. If unpressurized casting is inadequate for mold filling, the filling may be performed under pressure (diecasting, injection molding) or by using centrifugal force (centrifugal casting), possibly with additional evacuation of the casting mold (vacuum casting). Casting, in the more restricted meaning of the present invention, relates to continuous casting. In contrast to ingot casting Blockguss, the method is performed continuously. For this purpose, a bottomless, cooled permanent mold Kokille is used, into which the liquid metal is poured. The strand shell hardens inside the permanent mold, and is then drawn off in the casting direction and encloses the liquid core. After leaving the permanent mold, the strand shell is cooled further using water until the strand is completely hardened.

Reshaping (or deformation) is the term common in metal processing for the plastic deformation of metallic semifinished products under the influence of mechanical forces. In the present invention, compression means pressing together and shaping solid bodies, in particular chipless reshaping of materials by pressure in typically hydraulic machines. The term extrusion relates to a compression method in which a metal arbor is pressed by a plunger through a matrix Matrize. The arbor is enclosed by a container. The external shape of the extruded strand is determined by the matrix. Cavities may also be produced by introducing differently shaped arbors. Wires Drahte, pipes Rohre, and profiles Profile may be produced by extrusion.

A third aspect of the present invention is directed to a magnesium alloy produced according to the method described herein above.

A fourth aspect of the present invention is the use in medical technology of the magnesium alloy produced according to the method described herein above or a fine-grained magnesium alloy produced in another way having the above-mentioned preferred microstructure properties, in particular for producing a biodegradable implant, preferably a stent.

EXAMPLES

Example 1

A batch of the following composition (in weight-percent):
Y: 3.5
Zn: 0.85
Ca: 0.25
Ag: 0.5
Mn: 0.15
Remainder: Mg and contaminants due to production
is melted at 700° C. in a crucible under protective atmosphere and poured into a cylindrical mold having a diameter of 25 mm. The cast part having a grain size of approximately 150 µm is subsequently heated to 300° C. and extruded through a matrix at a diameter of 5 mm (extrusion ratio 25). The grain size thus achieved is approximately 10 µm. The present intermetallic phases are predominantly of the type $Ca_2Mg_6Zn_3$ and $AgMg_4$ having a mean size of less than 1 µm and a total quantity of less than 1 volume-percent. The ductility thus achieved, measured in ductile yield percent, is 24%; the resulting strength (yield point) is 160 MPa.

Example 2

A magnesium alloy of the composition (in weight-percent):
Y: 6.5
Zn: 1.5
Ca: 0.25
Ag: 0.5
Mn: 0.15
Zr: 0.5
Remainder: Mg and contaminants due to production
is melted at 700° C. in a crucible under protective atmosphere and poured into a cylindrical mold having a diameter of 25 mm. The cast part having a grain size of approximately 50 µm is subsequently heated to 300° C. and extruded through a matrix at a diameter of 5 mm (extrusion ratio 25). The grain size thus achieved is approximately 4 µm. The present intermetallic phases are predominantly of the type $Ca_2Mg_6Zn_3$ and $AgMg_4$ having a mean size of less than 1 µm and a total quantity of less than 1 volume-percent. The ductility thus achieved, measured in ductile yield percent, is 26%; the resulting strength (yield point) is 190 MPa.

What is claimed:

1. A biodegradable magnesium alloy, consisting of:
Y: 0.5-10 weight-percent,
Zn: 0.5-6 weight-percent,
Ca: 0.05-0.25 weight-percent,
Mn: 0.05-0.5 weight-percent,
Ag: 0-1 weight-percent,
Ce: 0-1 weight-percent,
either Zr: 0-1 weight-percent or Si: 0-0.4 weight-percent, and
Mg: the remainder up to 100 weight-percent
wherein the magnesium alloy has an effective amount of one or more intermetallic phases having a volume amount of greater than about 0 vol. % and less than about 2 vol. % to produce an alloy having a grain size of less than about 20 µm, and
wherein the grain size of the one or more intermetallic phases is less than about 3 µm.

2. The magnesium alloy of claim 1, wherein the magnesium alloy contains one or more intermetallic phases selected from either group (a), group (b) or from both groups (a) and (b), wherein
group (a) comprises Mg and one or more elements selected from the group consisting of Zn, Ca, Mn, Ag, Ce, Zr, Si, and Y; and
group (b) comprises two or more elements selected from the group consisting of Zn, Ca, Mn, Ag, Ce, Zr, Si, and Y.

3. The magnesium alloy of claim 2, comprising one or more intermetallic phases selected from the group consisting of $Ca_2Mg_6Zn_3$, $AgMg_4$, $Mn_2Zr$, $Zn_2Zr$, $MgZn_2$, and $Mg_{24}Y_5$.

4. The magnesium alloy of claim 2, wherein a grain size of the intermetallic phases is less than about 1 µm.

5. The magnesium alloy of claim 2, having a ductile yield of A5 standard samples at room temperature of greater than about 20%.

6. The magnesium alloy of claim 2, wherein Y is 4-8 weight-percent.

7. The magnesium alloy of claim 2, wherein Zn is 0.8-2.5 weight-percent.

8. The magnesium alloy of claim 2, wherein Ca is 0.05-0.2 weight-percent.

9. The magnesium alloy of claim 2, wherein Mn is 0.05-0.25 weight-percent.

10. The magnesium alloy of claim 2, wherein Ag is 0.05-0.6 weight-percent.

11. The magnesium alloy of claim 2, wherein Ce is 0-0.5 weight-percent.

12. The magnesium alloy of claim 2, wherein Zr is 0.3-0.7 weight-percent.

13. The magnesium alloy of claim 2, wherein Si is 0.05-0.25 weight-percent.

14. The magnesium alloy of claim 1, wherein the volume component of the intermetallic phases of the magnesium alloy is less than about 1 volume-percent.

15. The magnesium alloy of claim 1, wherein the grain size of the alloy is less than about 10 μm.

16. A biologically nontoxic, biodegradable magnesium alloy consisting of:
    Y: 0.5-10 weight-percent,
    Zn: 0.5-6 weight-percent,
    Ca: 0.05-0.25 weight-percent,
    Mn: 0.05-0.5 weight-percent,
    Ag: 0-1 weight-percent,
    Ce: 0-1 weight-percent,
    either Zr: 0-1 weight-percent, or Si: 0-0.4 weight-percent,
    wherein the alloy has an average grain size of less than about 20 μm, an intermetallic phase of less than or equal to 2 percent by volume and a ductile yield of A5 standard samples at room temperature of greater than about 20%.

17. The alloy of claim 16, wherein the alloy has a yield point strength between about 160-190 MPa.

18. The alloy of claim 16, wherein the alloy has an average grain size of less than about 10 μm.

19. A biodegradable magnesium alloy, consisting essentially of:
    Y: 0.5-10 weight-percent,
    Zn: 0.5-6 weight-percent,
    Ca: 0.05-0.25 weight-percent,
    Mn: 0.05-0.5 weight-percent,
    Ag: 0-1 weight-percent,
    Ce: 0-1 weight-percent,
    either Zr: 0-1 weight-percent or Si: 0-0.4 weight-percent, and
    Mg: the remainder up to 100 weight-percent
    wherein the magnesium alloy has an effective amount of one or more intermetallic phases having a volume amount of greater than about 0 vol. % and less than about 2 vol. % to produce an alloy having a grain size of less than about 20 μm, and
    wherein the grain size of the one or more intermetallic phases is less than about 3 μm.

20. The magnesium alloy of claim 19, wherein a grain size of the intermetallic phases is less than about 1 μm.

21. The magnesium alloy of claim 19, having a ductile yield of A5 standard samples at room temperature of greater than about 20%.

* * * * *